(12) United States Patent
Laurencin et al.

(10) Patent No.: US 8,614,189 B2
(45) Date of Patent: Dec. 24, 2013

(54) CARBON NANOTUBE COMPOSITE SCAFFOLDS FOR BONE TISSUE ENGINEERING

(75) Inventors: Cato T. Laurencin, Avon, CT (US); Syam Prasad Nukavarapu, New Britain, CT (US); Sangamesh G. Kumbar, South Windsor, CT (US)

(73) Assignee: University of Connecticut, Farmington, CT (US)

( * ) Notice: Subject to any disclaimer, the term of this patent is extended or adjusted under 35 U.S.C. 154(b) by 327 days.

(21) Appl. No.: 12/586,345

(22) Filed: Sep. 21, 2009

(65) Prior Publication Data

US 2010/0075904 A1 Mar. 25, 2010

Related U.S. Application Data

(60) Provisional application No. 61/099,762, filed on Sep. 24, 2008.

(51) Int. Cl.
*A61P 19/08* (2006.01)
*A61K 38/18* (2006.01)
*A61F 2/28* (2006.01)

(52) U.S. Cl.
USPC ..... 514/16.7; 514/7.6; 623/23.72; 623/23.73; 977/742; 977/745; 977/748; 977/752; 977/753; 977/778; 977/904; 977/908

(58) Field of Classification Search
None
See application file for complete search history.

(56) References Cited

U.S. PATENT DOCUMENTS

| | | | |
|---|---|---|---|
| 4,097,935 A | 7/1978 | Jarcho | |
| 4,131,597 A | 12/1978 | Bluethgen et al. | |
| 4,192,021 A | 3/1980 | Deibig et al. | |
| 4,223,412 A | 9/1980 | Aoyagi et al. | |
| 4,356,572 A | 11/1982 | Guillemin et al. | |
| 4,629,464 A | 12/1986 | Takata et al. | |
| 4,655,777 A | 4/1987 | Dunn et al. | |
| 4,698,375 A | 10/1987 | Dorman et al. | |
| 4,842,604 A | 6/1989 | Dorman et al. | |
| 5,032,129 A | 7/1991 | Kurze et al. | |
| 5,266,476 A | 11/1993 | Sussman et al. | |
| 5,514,181 A | 5/1996 | Light et al. | |
| 5,543,209 A | 8/1996 | Duquet et al. | |
| 5,595,621 A | 1/1997 | Light et al. | |
| 5,626,861 A | 5/1997 | Laurencin et al. | |
| 5,629,009 A | 5/1997 | Laurencin et al. | |
| 5,755,809 A | 5/1998 | Cohen et al. | |
| 5,766,618 A | 6/1998 | Laurencin et al. | |
| 5,866,155 A | 2/1999 | Laurencin et al. | |
| 6,017,366 A | 1/2000 | Berman | |
| 6,120,789 A | 9/2000 | Dunn et al. | |
| 6,136,029 A | 10/2000 | Johnson et al. | |
| 6,228,111 B1 | 5/2001 | Törmälä | |
| 6,308,509 B1 | 10/2001 | Scardino et al. | |
| 6,333,311 B1 | 12/2001 | Nuijens et al. | |
| 6,451,059 B1 | 9/2002 | Janas et al. | |
| 6,592,814 B2 | 7/2003 | Wilcox et al. | |
| 6,743,446 B2 * | 6/2004 | Schwendeman et al. | 424/486 |
| 7,122,057 B2 | 10/2006 | Beam et al. | |
| 7,163,557 B2 | 1/2007 | D'Eredità | |
| 7,235,295 B2 | 6/2007 | Laurencin et al. | |
| 7,241,486 B2 | 7/2007 | Pirhonen | |
| 7,250,550 B2 | 7/2007 | Overby et al. | |
| 7,323,442 B2 | 1/2008 | Yajima et al. | |
| 7,351,262 B2 | 4/2008 | Bindseil et al. | |
| 7,524,814 B2 | 4/2009 | Engelmayer et al. | |
| 2002/0111295 A1 | 8/2002 | Yajima et al. | |
| 2003/0191193 A1 | 10/2003 | Cornish et al. | |
| 2004/0191292 A1 | 9/2004 | Chou | |
| 2005/0079470 A1 * | 4/2005 | Rutherford et al. | 433/226 |
| 2005/0100581 A1 | 5/2005 | Laurencin et al. | |
| 2005/0169882 A1 | 8/2005 | Lowe et al. | |
| 2006/0263417 A1 | 11/2006 | Lelkes et al. | |
| 2007/0061015 A1 | 3/2007 | Jensen et al. | |
| 2007/0077267 A1 | 4/2007 | Molz, IV et al. | |
| 2007/0083268 A1 | 4/2007 | Teoh et al. | |
| 2007/0269481 A1 | 11/2007 | Li et al. | |
| 2008/0188644 A1 | 8/2008 | Cornish et al. | |
| 2008/0220042 A1 | 9/2008 | Hashi et al. | |
| 2008/0249638 A1 | 10/2008 | Asgari | |
| 2009/0028921 A1 | 1/2009 | Arinzeh | |
| 2009/0061152 A1 | 3/2009 | DeSimone et al. | |
| 2009/0068244 A1 | 3/2009 | Weber et al. | |
| 2009/0130191 A1 | 5/2009 | Ishikado et al. | |
| 2009/0169594 A1 | 7/2009 | Polizu et al. | |
| 2009/0253627 A1 | 10/2009 | Engelmayer et al. | |
| 2009/0259025 A1 | 10/2009 | Cornish et al. | |
| 2009/0281029 A1 | 11/2009 | Nojima et al. | |
| 2010/0310623 A1 | 12/2010 | Laurencin et al. | |

FOREIGN PATENT DOCUMENTS

| | | | |
|---|---|---|---|
| EP | 1 426 066 A1 | | 6/2004 |
| WO | WO2008/100534 | * | 8/2008 |
| WO | WO 2010/141718 A1 | | 12/2010 |

OTHER PUBLICATIONS

Wang et al., Biomacromolecules, 2005, vol. 6:3067-3072.*
Baek et al., Colloids and Surfaces A: Physicochem. Eng. Aspects, vol. 316:292-296.*
Kim et al., Langmuir, 2004, vol. 20:8239-8242.*

(Continued)

*Primary Examiner* — Xiaozhen Xie

(74) *Attorney, Agent, or Firm* — McDonnell Boehnen Hulbert & Berghoff LLP

(57) ABSTRACT

The present invention provides biocompatible composite materials that can be fabricated into a scaffold having properties suitable for bone repair and regeneration. These scaffolds have sufficient mechanical strength to be useful for the repair and regeneration of cortical bone.

16 Claims, 4 Drawing Sheets
(4 of 4 Drawing Sheet(s) Filed in Color)

(56) References Cited

OTHER PUBLICATIONS

Chun et al., Biotechnology Progress, 2004, vol. 20(6):1797-1801.*
Zhang et al., Nanotechnology, 2008, vol. 19, 395702, pp. 1-6.*
Abarrategi, A., et al., "Multiwall Carbon Nanotube Scaffolds for Tissue Engineering Purposes," *Biomaterials* 29:94-102 (2008).
Armentano, I., et al. "Effects of carbon nanotubes (CNTs) on the processing and in-vitro degradation of poly (DL-lactide-co-glycolide)/CNT films," *J Mater Sci: Mater Med* 19:2377-2387 (2008).
Barnes, C.P., et al., "Nanofiber Technology: Designing the Next Generation of Tissue Engineering Scaffolds," *Advanced Drug Delivery Reviews* 59:1413-1433 (2007).
Boonsongrit, Y., et al., "Controlled Release of Bovine Serum Albumin From Hydroxyapatite Microspheres for Protein Delivery System," *Materials Science and Engineering B* 148:162-165 (2008).
Borden, M., et al., "Structural and Human Cellular Assessment of a Novel Microsphere-based Tissue Engineered Scaffold for Bone Repair," *Biomaterials* 24:597-609 (2003).
Borden, M., et al., "The Sintered Microsphere Matrix for Bone Tissue Engineering: In Vitro osteoconductivity Studies," *J Biomed Mater Res* 61:421-429 (2002).
Borden, M., et al., "Tissue Engineered Microsphere-based Matrices for Bone Repair: Design and Evaluation," *Biomaterials* 23:551-559 (2002).
Boyan, B.D., et al., "Mechanisms Involved in Osteoblast Response to Implant Surface Morphology," *Annu. Rev. Mater. Res.* 31:357-371 (2001).
Boyan, B.D., et al., "Role of Material Surfaces in Regulating Bone and Cartilage Cell Response," *Biomaterials* 17:137-146 (1996).
Cai, K., et al., "Surface Modification of titanium Thin Film With Chitosan via Electrostatic Self-Assembly Technique and its Influence on Osteoblast Growth Behavior," *J Mater Sci: Mater Med* 19:499-506 (2008).
Chen, G.-X., et al., "Controlled Functionalization of Multiwalled Carbon Nanotubes with Various Molecular-Weight Poly(L-lactic acid)," *J. Phys. Chem. B* 109:22237-22243 (2005).
Chlopek, J., et al., "In Vitro Studies of Carbon Nanotubes Biocompatibility," *Carbon* 44:1106-1111 (2006).
Correa-Duarte, M.A., et al., Fabrication and Biocompatibility of Carbon Nanotube-Based 3D Networks as Scaffolds for Cell Seeding and Growth, *Nano Letters* 4(11):2233-2236 (2004).
Cuddihy, M.J. and Kotov, N.A., "Poly(lactic-co-glycolic acid) Bone Scaffolds with Inverted Colloidal Crystal Geometry," *Tissue Engineering: Part A* 14(10):1639-1649 (2008).
Descamps, M., et al., "Manufacture of Macroporous β-Tricalcium Phosphate Bioceramics," *Journal of the European Ceramic Society* 28:149-157 (2008).
Devin, J.E., et al., "Three-Dimensional Degradable Porous Polymer-Ceramic Matrices For Use In Bone Repair," *J. Biomater. Sci. Polymer Edn*, 7(8):661-669 (1996).
Edwards, S.L., et al., "Tubular micro-scale multiwalled carbon nanotube-based scaffolds for tissue engineering," *Biomaterials* 30:1725-1731 (2009).
Erisken, C., et al., "Functionally Graded Electrospun Polycaprolactone and β-Tricalcium Phosphate Nanocomposites for Tissue Engineering Applications," *Biomaterials* 29:4065-4073 (2008).
Fujihara, K., et al., "Guided Bone Regeneration Membrane Made of Polycaprolactone/Calcium Carbonate Composite Nano-Fibers," *Biomaterials* 26:4139-4147 (2005).
Gauthier, O., et al., "Kinetic Study of Bone Ingrowth and Ceramic Resorption Associated With the Implantation of Different Injectable Calcium-Phosphate Bone Substitutes," *J Biomed Mater Res* 47:28-35 (1999).
Glenn, G.M., et al., "Controlled Release of 2-Heptanone Using Starch Gel and Polycaprolactone Matrices and Polymeric Films," *Polym. Adv. Technol.* 18:636-642 (2007).
Gombotz, W.R., et al., "Stimulation of Bone Healing by TransformingGrowth Factor-Beta1 Released from Polymeric or Ceramic Implants," *J. Applied Biomaterials* 5:141-150 (1994).

Harrison, B.S., and Atala, A., "Carbon Nanotube Applications for Tissue Engineering," *Biomaterials* 28:344-353 (2007).
Heilmann, F., et al., "Development of Graded Hydroxyapatite/$CaCO_3$ Composite Structures for Bone Ingrowth," *J Mater Sci: Mater Med* 18:1817-1824 (2007).
Hosseinkhani, H., et al., "Bone Regeneration Through Controlled Release of Bone Morphogenetic Protein-2 from 3-D Tissue Engineered Nano-Scaffold," *Journal of Controlled Release* 117:380-386 (2007).
Huang, Y.X., et al., "Preparation and Properties of Poly(lactide-co-glycolide) (PGLA)/Nano-Hydroxyapatite (NHA) Scaffolds by Thermally Induced Phase Separation and Rabbit MSCs Culture on Scaffolds," *J Biomater Appl* 22:409-432 (Mar. 2008).
Jell, G., et al., "Carbon Nanotube-Enhanced Polyurethane Scaffolds Fabricated by Thermally Induced Phase Separation," *J Mater Chem* 18:1865-1872 (2008).
Jones, J.R., et al., "Quantifying the 3D Macrostructure of Tissue Scaffolds," *J Mater Sci: Mater Med* 20:463-471 (2009).
Karande, T.S., et al., "Diffusion in Musculoskeletal Tissue Engineering Scaffolds: Design Issues Related to Porosity, Permeability, Architecture, and Nutrient Mixing," *Annals of Biomedical Engineering* 32(12):1728-1743 (2004).
Khan, Y, et al., "Tissue Engineering of Bone; Material and Matrix Considerations," *J Bone Joint Surg Am* 90(suppl 1):36-42 (2008).
Kofron, M.D., et al., "Novel Tubular Composite Matrix for Bone Repair," *J Biomed Mater Res* 82A:415-425 (2007).
Kong, L., et al., "Preparation and Characterization of a Multilayer Biomimetic Scaffold for bone Tissue Engineering," *J Biomater Appl* 00:1-17 (2007).
Kumar, P.R.A., et al., "Alternate Method for Grafting Thermoresponsive Polymer for Transferring In Vitro Cell Sheet Structures," *J Appl Polym Sci* 105:2245-2251 (2007).
Kumar, P.R.A., et al., "Rapid and Complete Cellularization of Hydroxyapatite for Bone Tissue Engineering," *Acta Biomaterialia* 1:545-552 (2005).
Laffargue, PH., et al., "Evauliation of Human Recombinant Bone Morphogenetic Protein-2-Loaded Tricalcium Phosphate Implants in Rabbits' Bone Defects," *Bone* 25(suppl 2):55S-58S (1999).
Laurencin, C.T., et al., "A Highly Porous 3-Dimentional Polyphosphazene Polymer Matrix for Skeletal Tissue Regeneration," *J Biomedical Materials Research* 30:133-138 (1996).
Lyckfeldt, O. and Ferreira, J.M.F., "Processing of Porous Ceramics by 'Starch Consolidation'", *J European Ceramic Society* 18:131-140 (1998).
MacDonald, R.A., et al., "Collagen-Carbon Nanotube Composite Materials as Scaffolds in Tissue Engineering," *J Biomed Mater Res* 74A:489-496 (2005).
Matsuda, N., et al., "Tissue Engineering Based on Cell Sheet Technology," *Adv. Mater.* 19:3089-3099 (2007).
McIntosh, L., et al., "Impact of Bone Geometry on Effective Properties of Bone Scaffolds," *Acta Biomaterialia* 5:680-692 (2009).
Murugan, R., et al., "Nanofibrous Scaffold Engineering Using Electgrospinning," *J. Nanosci Nanotechnol* 7:4595-603 (2007).
Pham, Q.P., et al., "Electrospun Poly(ε-caprolactone) Microfiber and Multilayer Nanofiber/Microfiber Scaffolds: Characterization of Scaffolds and Measurement of Cellular Infiltration," *Biomacromolecules* 7:2796-2805 (2006).
Price, R.L., et al., "Selective Bone Cell Adhesion on Formulations Containing Carbon Nanofibers," *Biomaterials* 24:1877-1887 (2003).
Quinn, J.F. and Caruso, F., "Stabilization of Hydrogen-Bonded Poly(N-isopropylacrylamide) Multilayers by a Dual Electrostatic/Hydrogen Bonding Copolymer," *Aust. J. Chem.* 58:442-446 (2005).
Ren, Li-L., et al., "A Novel Strategy for Prefabrication of Large and Axially Vascularized Tissue Engineered Bone by Using an Arteriovenous Loop," *Medical Hypotheses* 71:737-740 (2008).
Rezwan, K., et al., "Biodegradable and Bioactive Porous Polymer/Inorganic Composite Scaffolds for Bone Tissue Engineering," *Biomaterials* 27:3413-3431 (2006).
Ritger, P.L. and Peppas, N.A., "A Simple Equation for Description of Solute Release I. Fickian and Non-Fickian Release From Non-Swellable Devices in the Form of Slabs, Spheres, Cylinders or Discs," *J. of Controlled Release* 5:23-36 (1987).

(56) References Cited

OTHER PUBLICATIONS

Salvetat, J.-P., et al., "Mechanical Properties of Carbon Nanotubes," *Appl Phys A* 69:255-260 (1999).

Schmidmaier, G., et al., "Biodegradable Poly(D,L-Lactide) Coating of Implants for Continuous Release of Growth Factors," *J Biomed Mater Res* 58:449-455 (2001).

Shi, X., et al., "Fabrication of Porpus Ultra-Short Single-Alled Carbon Nanotube Nanocomposite Scaffolds for Bone Tissue Engineering," *Biomaterials* 28:4078-4090 (2007).

Shi, X., et al., Injectable Nanocomposites of Single-Walled Carbon Nanotubes and Biodegradable Polymers for Bone Tissue Engineering, *Biomacromolecules* 7:2237-2242 (2006).

Silva, M.M.C.G., et al., "The Effect of Anisotropic Architecture on Cell and Tissue Infiltration Into Tissue Engineering Scaffolds," *Biomaterials* 27:5909-5917 (2006).

Sitharaman, B., et al., "In Vivo Biocompatibility of Ultra-Short Single-Walled Carbon Nanotube/Biodegradable Polymer Nanocomposites for Bone Tissue Engineering," *Bone* 43:362-370 (2008).

Smith, L.A. and Ma., P.X., "Nano-Fibrous Scaffolds for Tissue Engineering," *Colloids and Surfaces B: Biointerfaces* 39:125-131 (2004).

Soriano, I. and Évora, C., "Formulation of Calcium Phosphates/poly (d,l-lactide) Blends Containing Gentamicin for Bone Implantation," *J Controlled Release* 68:121-134 (2000).

Stevens, M.M., "Biomaterials for bone tissue engineering," *Materialstoday* 11(5):18-25 (2008).

Sun, Jui-S., et al., "The Effects of Calcium Phosphate Particles on the Growth of Osteoblasts," *J Biomed Mater Res* 37:324-334 (1997).

Supronowicz, P.R., et al., "Novel Current-Conducting Composite Substrates for Exposing Osteoblasts to Alternating Current Stimulation," *J Biomed Mater Res* 59:499-506 (2002).

Tang, Z., et al., "Biomedical Applications of Layer-by-Layer Assembly: From Biomimetics to Tissue Engineering," *Adv Mater* 18:3203-3224 (2006).

Teng, S-H., et al., "Collagen/Hydorxyapatite Composite Nanofibers by Electrospinning," *Materials Letters* 62:3055-3058 (2008).

Thoma, K., et al., "Biodegradable Controlled Release Implants Based on β-Tricalcium Phosphate Ceramic," *Eur. J. Pharm., Biopharm.* 38(3):107-112 (1992).

Tsuruga, E., et al., "Pore Size of Porous Hydroxyapatite as the Cell-Substratum Controls BMP-Induced Osteogenesis," *J. Biochem.* 121:317-324 (1997).

Valentini, L., et al., "Frequency Dependent Electrical Transport Between Conjugated Polymer and Single-Walled Carbon Nanotubes," *Diamond and Related Materials* 12:1601-1609 (2003).

Valmikinathan, C.M., et al., "Novel Nanofibrous Sprial Scaffolds for Neural Tissue Engineering," *J. Neural Eng*, 5:422-432 (2008).

Venugopal, J., et al., "Mineralization of Osteoblasts With Electrospun Collagen/Hydroxyapatite Nanofibers," *J Mater Sci: Mater Med* 19:2039-2046 (2008).

Verdejo, R., et al., "Reactive Polyurethane Carbon Nanotube Foams and Their Interactions With Osteoblasts," *J Biomed Mater Res* 88A:65-73 (2009).

Wang, J., et al., "Enhanced Osteoblast Response to 3D Sprial Nanofibrous Scaffolds in Rotating Wall Vessel (RWV) Bioractors," Annual Conference of Orthopedics Research Society (ORS), Las Vegas, NV, Feb. 2009.

Wang, J., et al., "Spiral-Structured, Nanofibrous, 3D Scaffolds for Bone Issue Engineering," *J Biomed Mater Res* 00A:1-11 (2009).

Wang, J., et al., "The Effect of Fiber Layer Thickness on the Bioactivity of Nanofibrous 3D Scaffolds for Bone Tissue Engineering," Annual Conference & Exposition of TERMIS, San Diego, CA, Dec. 2008.

Wang, J., et al., "The Influence of Fiber Thickness, Wall Thickness and Gap Distance on the Sprial Nanofibrous Scaffolds for Bone Tissue Engineering," *Mater. Sci. Eng.* C:1-7 (2009).

Wang, S.-F., et al., "Preparation and Mechanical Properties of Chitosan/Carbon Nanotubes Composites," *Biomacromolecules* 6:3067-3072 (2005).

Woo, K.M., et al., "Nano-Bibrous Scaffolding Promotes Osteoblast Differentiation and Biomineralization," *Biomaterials* 28:335-343 (2007).

Xu, S., et al., "RF Plasma Sputtering Deposition of Hydroxyapatite Bioceramics: Synthesis, Performance, and Biocompatibility," *Plasma Process. Polym.* 2:373-390 (2005).

Yang, J., et al., "Cell Delivery in Regenerative Medicine: The Cell Sheet Engineering Approach," *Journal of Controlled Release* 116:193-203 (2006).

Yang, J., et al., "Reconstruction of Functional Tissues With Cell Sheet Engineering," *Biomaterials* 28:5033-5043 (2007).

Yasuda, H.Y., et al., "Preparation of Hydroxyapatite/α-Tricalcium Phosphate Composites by Colloidal Process," *Science and Technology of Advanced Materials* 3:29-33 (2002).

Yu, H., et al., "Improved Tissue-Engineered Bone Regeneration by Endothelial Cell Mediated Vascularization," *Biomaterials* 30:508-517 (2009).

Zanello, L.P., et al., "Bone Cell Proliferation on Carbon Nanotubes," *Nano Letters* 6(3): 562-567 (2006).

Zhang, L. and Webster, T.J., "Nanotechnology and nanomaterials: Promises for improved tissue regeneration," *Nano Today* 4:66-80 (2009).

Zhang, X., et al., "Poly(vinyl alcohol/SWNT Composite Film," *Nano Letters* 3(9):1285-1288 (2003).

Notification of Transmittal of the International Search Report (ISR) and the Written Opinion (WO) of the International Searching Authority, or the Declaration, with copies of the ISR and WO, PCT/US2010/037256, mailed Jul. 21, 2010.

\* cited by examiner

CARBON NANOTUBE COMPOSITE SCAFFOLDS FOR BONE TISSUE ENGINEERING

RELATED APPLICATION

This application claims the benefit of U.S. Provisional Application No. 61/099,762, filed on Sep. 24, 2008.

The entire teachings of the above application are incorporated herein by reference.

BACKGROUND OF THE INVENTION

Trauma, pathological degeneration, or congenital deformity of tissues often requires surgical reconstruction or replacement. The defective tissues need to be replaced with viable, functioning alternatives. In skeletal applications, surgeons have historically used bone grafts, primarily autografts and allografts. However, both types of grafts have significant disadvantages. For example, there is the problem of donor site morbidity where damage occurs at the harvest site caused by removal of the graft. In addition, there is only a limited amount of bone available for harvesting. Furthermore, autografts have unpredictable resorption characteristics. With allografts there are the well-recognized problems associated with adverse immunologic responses to the foreign grafted tissue. As a result, newly grafted tissue is often rejected by the body and induces a severe inflammatory response. Allografts are also capable of transmitting diseases, despite pre-screening processes, since pre-screening is not 100% effective.

Conventional orthopedic implants such as screws, plates, pins and rods serve as load-bearing replacements for damaged bone and are usually composed of a metal or alloy. Although these implants are capable of providing rigid fixation and stabilization of the bone, they cause improper bone remodeling of the implant site due to the large difference in the modulus between bone and metal.

Alternative synthetic bone graft substitutes have been the subject of extensive research. Such bone graft substitutes need to be biocompatible, capable of supporting new bone growth, possess mechanical strength and preferably be biodegradable. However, despite the extensive research in this field, the synthetic bone graft substitutes often fail to meet all of these criteria. Thus, there is a need to provide a biocompatible composite materials that can be fabricated into a scaffold having properties suitable for bone repair and regeneration, and methods for making such materials.

SUMMARY OF THE INVENTION

The present invention provides biocompatible composite materials that can be fabricated into a scaffold having properties suitable for bone repair and regeneration. Unlike previously described materials, these scaffolds are biocompatible, biodegradable, and have sufficient mechanical strength to be useful for the repair and regeneration of cortical bones.

One aspect of the invention is a biocompatible composite material comprising functionalized carbon nanotubes and a biodegradable polymer. In one embodiment, the biocompatible composite material comprising functionalized carbon nanotubes and a biodegradable polymer does not comprise calcium phosphate. The biocompatible composite material comprises a low concentration of carbon nanotubes. The carbon nanotubes are functionalized such that the carbon nanotubes are water dispersible. For example, the carbon nanotubes can be functionalized with carboxyl groups, amide groups, hydroxyl groups, polyethylene glycol (PEG), or any combination thereof. In one embodiment, the carbon nanotubes are randomly dispersed in the composite material. In another embodiment, the carbon nanotubes are single wall carbon nanotubes. In another embodiment, the carbon nanotubes are multi-wall carbon nanotubes. In a further embodiment, the biodegradable polymer comprises, consists essentially of, or consists of poly(lactic acid-glycolic acid) (PLGA). The biodegradable polymer preferably has a microsphere shape.

Another aspect of the invention is a biocompatible composite scaffold material fabricated with the biocompatible composite material described herein. The scaffold material has a compressive modulus value and a compressive strength suitable for, and compatible with, repair and regeneration of load-bearing bone, such as cortical bone. In one embodiment, the biocompatible composite scaffold material has a compressive modulus value of at least about 200 MPa to at least about 500 MPa. Furthermore, the biocompatible composite scaffold material has a compressive strength of at least about 5.0 MPa to at least about 50 MPa. Preferably, the scaffold material is sufficiently porous to allow, for example, seeding and growth of cells. In one embodiment, the scaffold material has a porosity of at least about 25%-about 35%, preferably at least about 30% porosity.

In another aspect of the invention, the biocompatible composite material and/or biocompatible composite scaffold material further comprises one of more further agents. In one embodiment, the agent is a bioactive agent. For example, a bioactive agent is a bone morphogenic protein (BMP), a vascular endothelial growth factor (VEGF), a connective tissue growth factor (CTGF), osteoprotegerin, a growth differentiation factor (GDF), a cartilage-derived morphogenic protein (CDMP), a LIM mineralization protein (LMP), a transforming growth factor beta (TGFβ), an antibiotic, an immunosuppressive agent, or any combinations thereof.

A further aspect of the invention is a method of producing a biocompatible composite scaffold material. The method comprises dispersing functionalized carbon nanotubes with a biocompatible polymer in a solvent to produce a composite, such as the biocompatible composite material described herein. In one embodiment, ultrasonication is used to disperse the functionalized carbon nanotubes with a biocompatible polymer in a solvent. The composite is thermally sintered using a mold (e.g., a metallic mold) to produce the biocompatible composite scaffold material. In one embodiment, the biocompatible polymer are polymer microparticles. For example, the polymer microparticles can be microspheres. In another embodiment the biocompatible composite scaffold material has a compressive modulus value of at least about 250 MPa and a compressive strength of at least about 7.5 MPa. Another embodiment is a biocompatible composite scaffold material produced by the methods described herein.

A further aspect of the invention is a method of effecting bone repair or bone regeneration in a subject. The method comprises contacting the bone defect or area needing bone regeneration with a biocompatible composite scaffold material as described herein. In one embodiment, the bone in need of repair or regeneration is cortical bone.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8A Compressive data indicating a two fold increase in compressive modulus. FIG. 8B demonstrates a three fold increase in compressive strength for the composite scaffolds. The mechanical enhancement is attributed to the carbon nanotube reinforcement taking place more prominently at the microsphere-microsphere joining areas.

FIGS. 10(a) and (b) are SEM images showing (a) sintered PLGA matrix and (b) microsphere to microsphere contact region in the case of a composite scaffold. FIG. 10(c) schematically demonstrates the carbon nanotube network in a polymer matrix based on the observed scaffold mechanical enhancement data. The bonding regions in a 3D scaffold are mechanically weak points. Therefore, mechanical strength of a 3D scaffold is often limited by weak contact regions. As described herein the bonding regions are reinforced through water dispersible carbon nanotubes.

DETAILED DESCRIPTION OF THE INVENTION

Definitions

Figure 1:
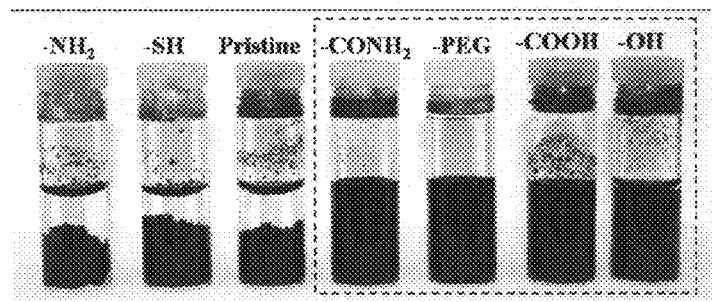
FIG. 1 demonstrates water dispersibility of functionalized carbon nanotubes (FNCTs). The carbon nanotubes were either non-functionalized (pristine) or functionalized with amine (—NH$_2$), thiol (—SH), amide (—CONH$_2$), polyethylene glycol (PEG), carboxyl (—COOH) or hydroxyl (—OH) groups. The pristine, amine, and thiol FCNTs exhibit sedimentation (demonstrating poor water dispersibility), while FCNTs with amide, PEG, carboxyl and hydroxyl groups resulted in uniform dispersion (demonstrating good water dispersibility).

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this specification pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes minor deviations. Such deviation can be the result of inherent variation from error for the device or the method being employed to determine the value.

As used herein, the following acronyms have the following definitions: CNT: carbon nanotube; SWNT or SWCNT: single-wall carbon nanotube; MWNT or MWCNT: multi-wall carbon nanotube; FCNT: functionalized carbon nanotube; PLGA: Poly(lactic acid-glycolic acid) (also sometimes referred to as PLAGA); PLA: poly lactic acid; PGA: poly glycolic acid; MPa: mega Pascal; SEM: Scanning Electron Microscopy.

Bone loss occurs mainly due to trauma, congenital defects, malignant diseases and primary and revision joint surgeries. The repair and replacement of damaged bone is a major clinical problem in the U.S. and world wide. In the U.S. alone over a million bone fractures or defects are treated each year, this number is expected to grow as the life expectancy increases and the overall U.S. population is continues to rise. Current bone replacement procedures often use autograft or allograft tissue, but these approaches have limitations. Autografts are often limited in supply and the harvest of these tissues is associated with donor site morbidity. Allografts carry the potential of disease transmission and immunological rejection. Therefore, there exists a need to develop bone graft substitute materials that could mimic the properties of bone while eliminating the shortcomings of traditional bone grafts such as autografts and allografts.

Synthetic bone graft substitutes (based on metals, polymers and ceramics) have been suggested as alternatives due to their unlimited supply, easy sterilization and storage. Currently available synthetic bone substitutes involve biodegradable polymers, and their composites with various forms of calcium phosphate with or without bioactive agents. These substitutes have attracted a lot of attention over metallic grafts, because of their transient nature and degradation into body friendly by-products. Composites of biodegradable polymers with hydroxyapatite improved mechanical strength while also improving osteocompatibility of the graft material. However, the existing bone graft materials still suffer from their weak mechanical properties compared to the bone tissue. Therefore, there is a strong need to develop biodegradable polymer composites with bone tissue comparable mechanical properties for bone grafting applications.

Bone tissue engineering is the application of biological, chemical, and engineering principles towards the repair, restoration or regeneration of tissues using cells, factors, and scaffolds alone or in combination. Scaffold based tissue engineering has become a promising strategy in bone tissue regeneration, because cells alone lack the ability to form three dimensional tissues without the support of an artificial structure referred to as a scaffold. An ideal scaffold should exhibit biocompatibility, biodegradability, mechanical compatibility, interconnected porosity and non-toxic degradation products.

Early efforts using polymeric biodegradable scaffolds demonstrate only weak load bearing ability which limits their clinical applicability for bone regeneration and repair application. Such scaffolds may be useful for other applications, such as nerve cell growth and the like. In contrast, the present invention provides biocompatible composite materials that can be fabricated into a scaffold having properties suitable for bone repair and regeneration. These scaffolds have sufficient mechanical strength to be useful for the repair and regeneration of cortical bone. Cortical bone, also referred to as compact bone, is one of the two types of osseous tissue that form bones (the other being cancellous bone). Cortical bone facilitates the main functions of bones, namely, support the body, protect organs, provide levers for movement, and store and release chemical elements, mainly calcium and phosphorous. Cortical bone forms the cortex, or outer shell, of most bones and is much denser than cancellous bone. Furthermore, cortical bone is harder, stronger and stiffer than cancellous bone.

Polymer-based materials have been utilized for the construction of medical devices for many years. Polymers are a class of synthetic materials characterized by their high versatility. The versatility has led to the development of biodegradable, biocompatible polymers created primarily for use in medical applications. One of the most common polymers used as a biomaterial has been the copolymer poly(lactic acid-glycolic acid) referred to herein as PLGA. PLGA is highly biocompatible, degrades into harmless monomer units and has a wide range of mechanical properties making this copolymer and its homopolymer derivatives, PLA and PGA, useful in medical applications.

Porous, three-dimensional matrices comprising these polymers for use in bone replacement have been prepared using various techniques. Coombes and Heckman (Biomaterials 1992 3:217-224) describe a process for preparing a microporous polymer matrix containing 50:50 PLGA:PLA and 25:75 PLA:PLGA. The polymer is dissolved in poor solvent with heat and the gel is formed in a mold as the polymer cools. Removal of the solvent from the matrix creates a microporous structure. However, the actual pore size of this matrix (<2 µm) is inadequate for bone ingrowth which requires a pore size falling within the range of 100-250 µm for cell growth to occur. Furthermore, polymers, such as PLGA, generally lack sufficient mechanical strength for use in bone repair and regeneration, particularly for cortical bone.

Carbon-based materials have also been the subject of extensive research for biological applications. Structures made of carbon materials have been investigated as substrates for cell scaffolding and growth. For example, carbon nanotube ("CNT") technology is being applied to medical applications, with recent investigations focusing on carbon nanotubes as substrates for the growth of retinal cells, neural cells and endothelial cells. Also, CNT-based composites have been investigated for cartilage regeneration and in vitro cell proliferation of chondrocytes. Carbon nanotubes are strong and are also capable of being shaped into 3D architectures and are promising in the construction of engineered products for biological applications. Carbon is an inert material and thus is generally biocompatible, however, recent studies have raised the concern that carbon nanotubes, so-called "pristine" CNTs have adverse health effects in the body.

Specific Embodiments

Described herein is a biocompatible composite material comprising water dispersible carbon nanotubes and a biodegradable polymer. Water-dispersible carbon nanotubes are carbon nanotubes that form a uniform dispersion or homogeneous suspension when mixed with water. In contrast, non-water-dispersible carbon nanotubes sediment or settle after mixing in water. Also described is a scaffold material suitable for use in bone growth and regeneration, as well as methods of making these compositions.

Thus, one aspect of the invention is a biocompatible composite material comprising water dispersible carbon nanotubes and a biodegradable polymer. In one embodiment, the biocompatible composite material comprising water dispersible carbon nanotubes and a biodegradable polymer does not comprise calcium phosphate.

Biodegradable polymers, both natural and synthetic, are well known in the art and include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials. Suitable biodegradable polymers can be chosen by the person skilled in the art using standard techniques and based on the mechanical and degradation properties of the polymer such that the polymer is chosen for its compatibility with bone regeneration.

Biodegradable polymers can be of any suitable form or shape. For example, the biodegradable polymer is a microparticle. In one embodiment, the biodegradable polymer is a microsphere. Such shapes of the biodegradable polymer is advantageous to the forming of pores or channels in a biocompatible composite scaffold material as described herein.

In one embodiment, the biodegradable polymer comprises, consists essentially of, or consists of poly(lactic acid-glycolic acid) (also referred to as poly(lactic-co-glycolic acid) or poly (lactide-co-glycolide)) (PLGA). In one embodiment, the PLGA is 85:15 PLGA (referring to the molar ratio of lactic acid to glycolic acid). In another embodiment, the PLGA is 50:50 PLGA, 65:35 PLGA, and the like.

The biocompatible composite material further comprises a low concentration of water-dispersible carbon nanotubes. In one embodiment, the carbon nanotubes are multi-wall carbon nanotubes. In another embodiment, the carbon nanotubes are single-wall carbon nanotubes. In an alternative embodiment, the carbon nanotubes are a mixture of single-wall and multi-wall carbon nanotubes. The concentration of carbon nanotubes is such that carbon nanotubes are not the majority component (e.g., less than about 50% (wt/wt), more preferably less than about 10% (wt/wt), still more preferably less than about 5% (wt/wt) of the composite material. In one embodiment, the biocompatible composite material comprises about 7%, 6%, 5%, 4%, 3%, 2%, 1%, 0.5% or less (wt/wt) carbon nanotubes. In a particular embodiment, the biocompatible composite material comprises about 1-4%, about 1-3%, about 2-3%, or about 2-4% (wt/wt) carbon nanotubes. As will be appreciated, the amount of carbon nanotubes optimally achieves the mechanical properties that are compatible for bone repair and regeneration, but which minimizes any potential side effects of the presence of carbon nanotubes in the body.

The carbon nanotubes can vary in size. In one embodiment, the carbon nanotubes are typically about 1-30 nm in diameter and typically about 0.5-30 µm in length. In one embodiment, the carbon nanotubes are about 1-10 nm, about 1-20 nm, about 5-10 nm, about 5-20 nm, about 5-30 nm, about 10-20 nm, about 10-30 nm, about 15-25 nm, about 15-30 nm, and/or about 20-30 nm in diameter. In another embodiment, the carbon nanotubes are about 0.5-1 µm, about 0.5-2 µm, about 0.5-3 µm, about 0.5-4 µm, about 0.5-5 µm, about 0.5-6 µm, about 0.5-7 µm, about 0.5-8 µm, about 0.5-9 µm, about 0.5-10 µm, about 0.5-15 µm, about 0.5-20 µm, about 0.5-25 µm, about 1-5 µm, about 1-10 µm, about 1-20 µm, about 1-30 µm, about 5-10 µm, about 5-20 µm, about 5-25 µm, about 5-30 µm, about 10-20 µm, about 10-25 µm, about 10-30 µm, and/or about 25-30 µm in length. As will be appreciated, the diameter and length of the carbon nanotubes can be varied to optimize the strength and properties of the biocompatible composite material described herein.

The carbon nanotubes are functionalized such that the carbon nanotubes are water dispersible. Such water dispersible functionalized carbon nanotubes have the added advantage of rapid and ease of clearance from the body, thereby alleviating potential toxic effects of carbon nanotubes. The carbon nanotubes can be functionalized with any suitable group. In one embodiment, carbon nanotubes are functionalized with carboxyl groups, amide groups, hydroxyl groups, polyethylene glycol (PEG), or any combination thereof. At least about 1-10%, 2-8%, 3-6%, or 4-5% of the carbon atoms in the carbon nanotubes are functionalized. In a preferred embodiment, at least about 4-5% of the carbon atoms in the carbon nanotubes are functionalized.

In one embodiment, the carbon nanotubes are randomly dispersed in the composite material. As described herein, in one embodiment, the carbon nanotubes are randomly dispersed on the surface of polymer microspheres.

Another aspect of the invention is a biocompatible composite scaffold material fabricated with the biocompatible composite material described herein. In one embodiment, the biocompatible composite scaffold material has a compressive modulus value of at least about 200 MPa to at least about 500 MPa. In another embodiment, the biocompatible composite scaffold material has a compressive modulus value of at least about 250 MPa, about 275 MPa, about 300 MPa, about 325 MPa, about 350 MPa, about 375 MPa, about 400 MPa, about 425 MPa, about 450 MPa, about 475 MPa, or about 500 MPa. In a further embodiment, the biocompatible composite scaffold material has a compressive modulus value of about 260±46 MPa. In a another embodiment, the biocompatible composite scaffold material has a compressive modulus value of about 371±27 MPa. Furthermore, the biocompatible composite scaffold material has a compressive strength of at least about 5.0 MPa to at least about 50 MPa. In one embodiment, the biocompatible composite scaffold material has a compressive strength of at least about 10 MPa, about 15 MPa, about 20 MPa, about 25 MPa, about 30 MPa, about 35 MPa, about 40 MPa, about 45 MPa, or about 50 MPa. In one embodiment, the biocompatible composite scaffold material has a compressive strength about 7.2±1.51 MPa. In another embodiment, the biocompatible composite scaffold material has a compressive strength about 25.7±1.8 MPa. The scaffold material is sufficiently porous to allow, for example, seeding and growth of cells. In one embodiment, the scaffold material has a porosity of at least about 25%-about 35%, preferably at least about 30% porosity.

In another aspect of the invention, the biocompatible composite material and/or biocompatible composite scaffold material further comprises one of more agents. Such agents can be, e.g., a bioactive agent, or an inert agent. Inert agents can be any suitable agent, e.g., carrier, excipient, sterilizing solution, labeling solution, and the like. Bioactive agents are also known in the art. For example, bone morphogenic proteins (BMP), vascular endothelial growth factors (VEGF), connective tissue growth factors (CTGF), osteoprotegerin, growth differentiation factors (GDFs), cartilage-derived morphogenic proteins (CDMPs), LIM mineralization proteins (LMPs), transforming growth factor beta (TGFβ), antibiotics, immunosuppressive agents, and combinations thereof. Additional, or alternative non-limiting examples of agents include collagen, drugs, antibodies, peptides, peptidomimetics, oligonucleotides, chemical entities, growth factors, and mixtures thereof.

Examples of bone morphogenic proteins (BMP) include: BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; and BMP-18. Vascular endothelial growth factors (VEGF) include VEGF-A, VEGF-B, VEGF-C, VEGF-D and VEGF-E. Connective tissue growth factors (CTGF) include CTGF-1, CTGF-2, and CTGF-4. Growth differentiation factors (GDFs) include GDF-1, GDF-2, GDF-3, GDF-7, GDF-10, GDF-11, and GDF-15. Cartilage-derived morphogenic proteins (CDMPs) include CDMP-1 and CDMP-2. LIM mineralization proteins (LMPs) include LMP-1, LMP-2, and LMP-3. Transforming growth factor beta (TGFβ) include TGFβ-1, TGFβ-2, and TGFβ-3.

Examples of antibiotics useful with the biocompatible composite material include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamethoxazole, and vancomycin.

Suitable immunosuppressive agents that can be included in the biocompatible composite material, include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™3 (muromonab-CD3) Sandimmune™, Neora™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

As will be appreciated by those in the art, bioactive agents can be polypeptides, including full length polypeptides, biologically active fragments thereof, and fusion proteins, small molecules, and cells expressing such bioactive agents. Furthermore, the concentrations of the bioactive agent can be variable based on the desired length or degree of activity required.

A further aspect of the invention is a method of producing a biocompatible composite scaffold material. The method comprises dispersing functionalized carbon nanotubes with a biocompatible microsphere polymer in a solvent to produce composite microspheres, such as the biocompatible composite material described herein. In one embodiment, ultrasonication is used to disperse the functionalized carbon nanotubes with a biocompatible microsphere polymer in a solvent. Non-limiting examples of a suitable solvent include acetone, dichloromethane, and mixtures thereof. The composite microspheres are cast in a suitable mold and then sintered to produce the biocompatible composite scaffold material. In one embodiment, the composite microspheres are sintered at about 95° C., about 100° C., or about 105° C. for about 1 hour. In another embodiment, the biocompatible composite scaffold material has a compressive modulus value of at least about 250 MPa and a compressive strength of at least about 7.5 MPa.

A further aspect of the invention is a method of effecting bone repair or bone regeneration in a subject. The method comprises contacting the bone defect or area needing bone regeneration with a biocompatible composite scaffold material as described herein. In one embodiment, the bone in need of repair or regeneration is cortical bone. Thus, in one embodiment is a method of performing a bone repair surgery on a patient whereby the area of the bone in need of repair or regeneration is accessed and cleaned, preferably using minimally invasive techniques. The biocompatible composite scaffold material is inserted and positioned in the appropriate area of the bone, and the incision is surgically closed.

EXEMPLIFICATION

Example 1

Water Dispersible Carbon Nanotubes (WDCNTs)

Carbon nanotubes (CNTs) were purchased from Cheap Tubes, Inc. (Vermont, USA). Various single and multi-wall functionalized carbon nanotubes were screened for their water dispersibility. 0.1% (wt/vol) of carbon nanotubes (functionalized or non-functionalized (so called "pristine")) were mixed with water and subjected to sonication for 1 h at room temperature. The suspension was allowed to stand for 24 h to observe any nanotube settlement. As shown in FIG. 1, carbon nanotubes functionalized with —$CONH_2$, poly ethylene glycol (PEG), —COOH and —OH groups exhibited good water-dispersibilty. In contrast, non-functionalized (pristine) carbon nanotubes and carbon nanotubes functionalized with —$NH_2$ and —$SH_2$ resulted in sedimentation.

Example 2

PLGA-Water Dispersible Carbon Nanotube Composite 2D-Matrices

Composite matrices with water dispersible carbon nanotubes (WDCNTs) (nanotubes with amide, poly ethylene glycol, carboxyl and hydroxyl as functional groups) were fabricated. Two dimensional matrices were studied for biocompatibility and osteocompatibility. The preparation of biodegradable polymers in two dimensional films have been described elsewhere (Deng, et al., 2008, 2009). Here, water dispersible carbon nanotube composites with poly(85-lactide-co-15-glycolide) (PLGA) was fabricated into two-dimensional films. Various WDCNTs (1 wt %) were mixed with PLGA in acetone and sonicated for 2 h. Acetone was selected as a solvent because it could solubilize PLGA while also interacting with hydrophilic nanotubes through dipolar interactions. Uniformly mixed solutions were cast and allowed a slow evaporation at 4° C. The solutions were subjected to constant agitation to prevent nanotube agglomeration. Dried films were bored into 10 mm diameter disks and used for biomineralization and in vitro osteoblast cell proliferation and differentiation studies.

Figure 2:
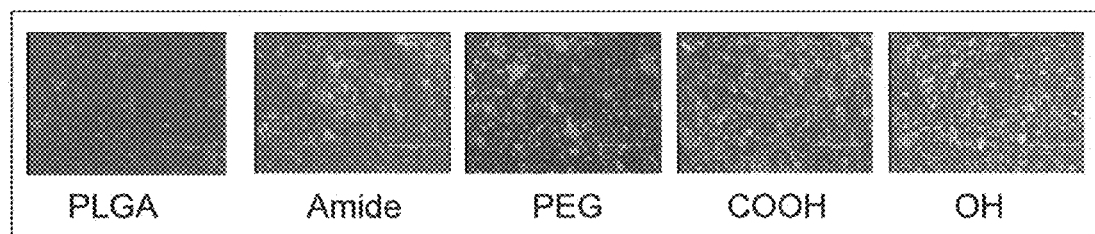
FIG. 2 is a series of photographs demonstrating the biomimetic nature of different water-dispersible FCNT-PLGA composites in simulated body fluid (SBF). Water-dispersible nanotubes (1% wt/wt) were mixed with PLGA 85/15 in acetone and sonicated for 2 hours. Composite films were cast and vacuum dried. Composite films were immersed in SBF for 7, 14 and 21 days. Mineral deposition was viewed using scanning electron microscopy (SEM). Shown are photographs at day 7. Composites showed increased levels of biomimetic mineral deposition, by day 7, as compared to the control PLGA.
Figure 3:
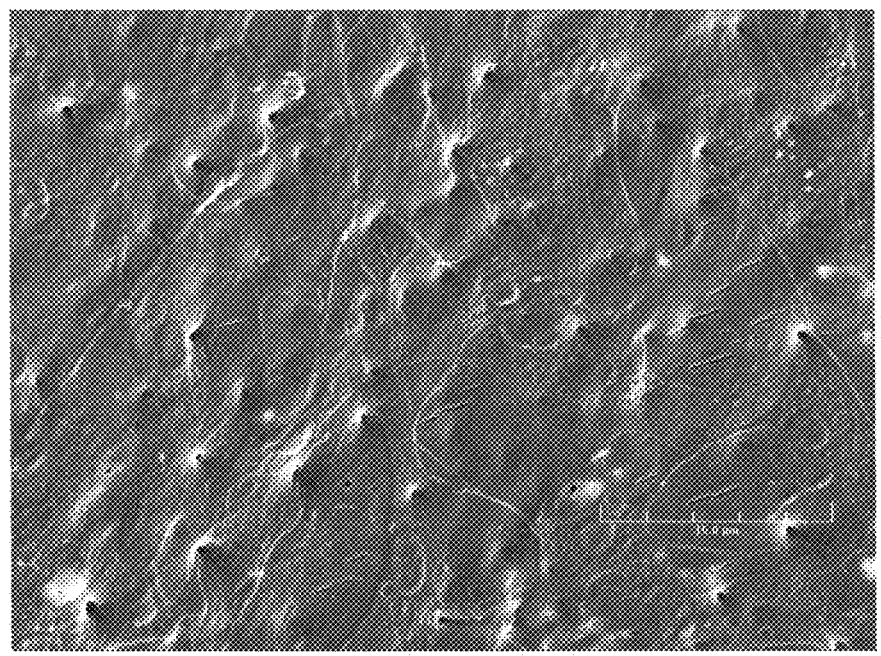
FIG. 3 is a representative SEM image showing MC3T3-E1 cell adhesion on a composite matrix of PLGA-1% CNT-COOH cultured for 10 days.

Biomineralization:

Hydroxyapatite layer formation on a biomaterial surface in simulated body fluid (SBF) is considered an early indication of a material's biocompatibility. In this example, all the composites were tested in SBF for their biocompatibility. Two dimensional matrices were immersed in SBF for 7, 14 and 21 days and the mineral deposition was analyzed using scanning electron microscopy (SEM). Carbon nanotube composites showed increased levels of biomimetic mineral deposition, by day 7, when compared to the control PLGA (FIG. 2). Increased bio-mineralization suggested carbon nanotube functional group interaction with the surrounding calcium and phosphate ions in SBF. Such interactions could have resulted in mineral phase nucleation and growth. Elemental analysis suggested the mineral phase as the desired calcium deficient hydroxyapatite. This study confirmed the enhanced biomineralization ability of the novel PLGA-water dispersible carbon nanotube composite biomaterials.

Figure 4:
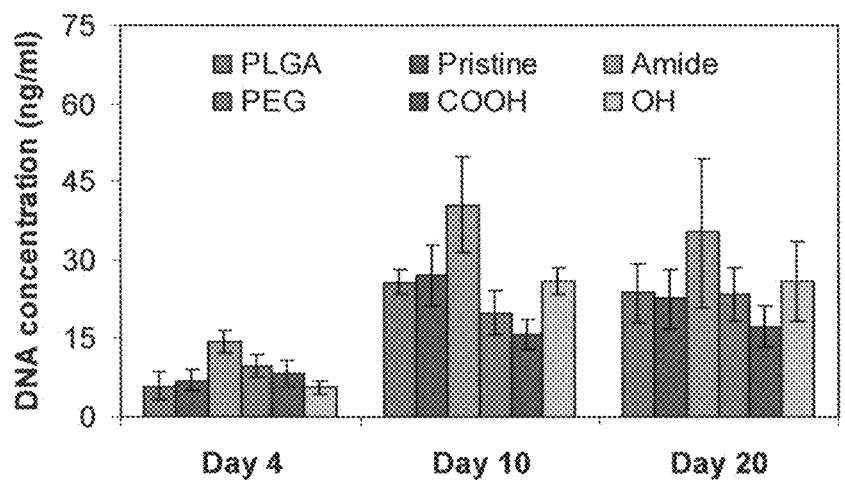
FIG. 4 is a graph charting pre-osteoblast (MC3T3-E1) cell proliferation (calculated using DNA quantification) on PLGA and PLGA-FCNT composite matrices.
Figure 5:
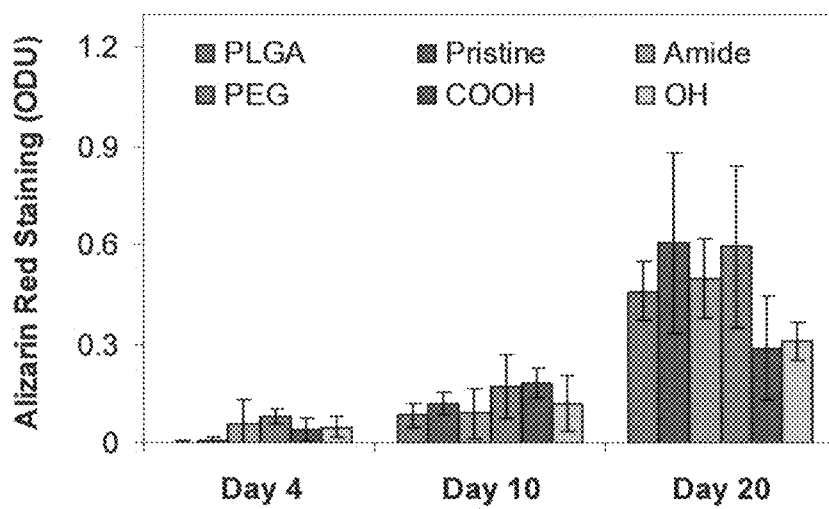
FIG. 5 is a graph charting pre-osteoblast (MC3T3-E1) cell differentiation and mineralization. Alizarin red was used to quantify calcium deposition by osteoblast mineralization on PLGA and PLGA-FCNT composite matrices.
Figure 6:
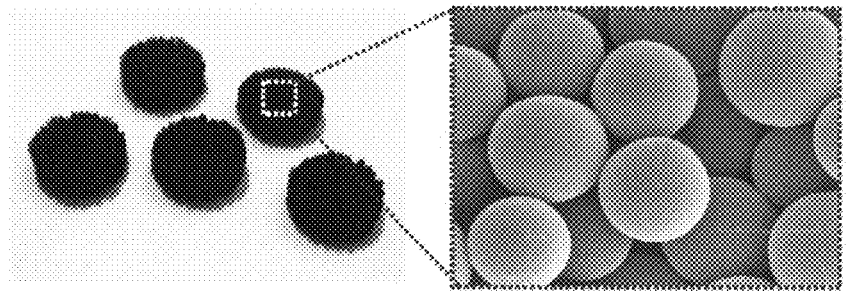
FIG. 6 is a photograph of PLGA-FCNT microsphere scaffolds sintered at 105° C./1 h, and a SEM micrograph of the PLGA microspheres loaded with 3% FCNTs.

Cell Proliferation and Osteocompatibility Evaluations (FIGS. 4 and 5):

Nanotube composites were further characterized for their cell compatibility. This study was designed to understand the bone cell interaction with functionalized carbon nanotubes. Mouse MC3T3-E1 osteoblasts were seeded onto two-dimensional composite matrices at a density of $5 \times 10^4$ cells per each rounded scaffold of 10 mm diameter. At days 4, 10 and 20, cellularized constructs were taken out of the culture and characterized for MC3T3-E1 adhesion and spreading (scanning electron imaging), proliferation (PicoGreen dsDNA assay), and calcium deposition (both Alizarin red staining and quantification). Cell adhesion and growth were quite similar to the observations made on PLGA polymer matrix. Composite matrices with amide functional nanotubes showed higher cell proliferation throughout the study. It was also clear that composite scaffolds exhibited higher levels of calcium deposition at the initial stage and the response was leveled by day 20. Observations were comparable to osteoblast performance with PLGA in terms of proliferation, and mineralization indicates the non-toxic nature of these functionalized carbon nanotube composites in vitro and their suitability for bone tissue engineering.

Example 3

Carbon Nanotube-PLGA Composite Microspheres and 3D-Scaffolds

PLGA-CNT composite microspheres were prepared and fabricated into three dimensional scaffolds which can then be used in bone regeneration. In this example, multi-wall carbon nanotubes functionalized with carboxylic groups were used (referred to herein as MWCNTs). These are 20-30 nm in diameter and 10-30 μm in length with 4-5% of carbons functionalized with —COOH groups. MWCNTs were considered because they are water dispersible like single-wall nanotubes, and can be easily visualized under SEM.

Figure 7:
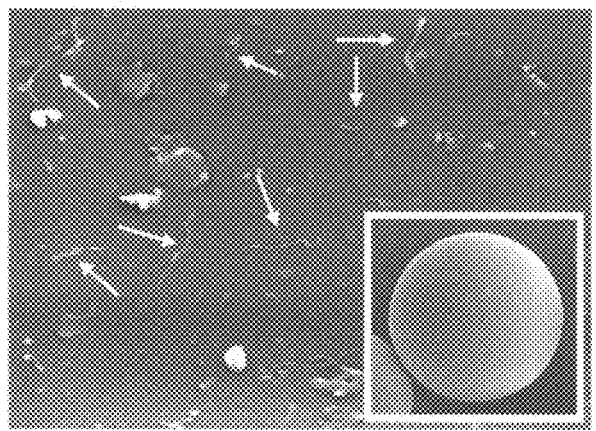
FIG. 7 is an SEM image. The arrows show the presence of carbon nanotubes on the microsphere surface. Insert shows the PLGA microsphere comprising of 3 wt % multi-wall carbon nanotubes functionalized with COOH groups. Nanotubes used in this study were of 20-30 nm outer diameter and 10-30 μm in length.

MWCNTs were added to polymer PLGA 85/15 (3% (wt/wt)), dissolved in methylene chloride and subjected to ultra-sonication for uniform nanotube dispersion. The polymer solution was formed into microspheres using a previously reported procedure (Biomacromolecules (2008) 9: 1818-25, the teachings of which are incorporated herein by reference) SEM investigations revealed the presence of carbon nanotubes (FIG. 7) on the microsphere surface. This was a significant observation, as carbon nanotubes available on the microsphere surface can participate in bonding with the adjacent microspheres during scaffold fabrication. Further, microspheres were sintered in a steel mold at a range of temperatures (95, 100, 105° C./1 h) to form three dimensional scaffolds. Sintered scaffolds were visualized under SEM to examine the microsphere-microsphere bonding. A typical microstructure of microspheres sintered at 100° C./1 h showed 3D-architecture with roughly 30% porosity which is desirable for bone defect repair and regeneration.

Figure 8:
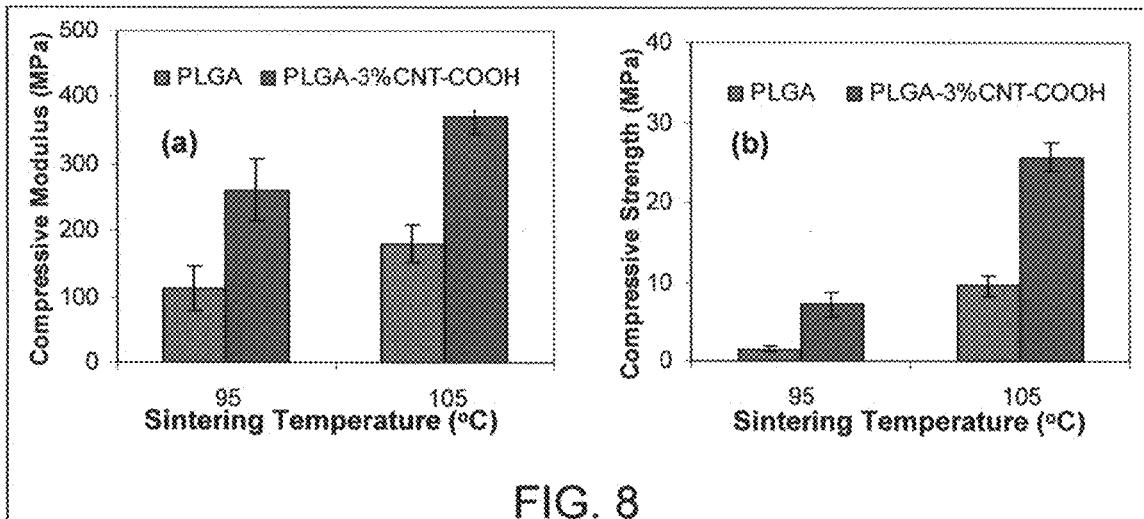
FIGS. 8A and 8B are graphs of the mechanical characterization of PLGA and PLGA-3% MWCNT-COOH composite scaffolds sintered at 95 and 105° C./1 h.

3D-Composite Scaffolds: Carbon Nanotube-Assisted Mechanical Reinforcement:

Scaffolds were formed by dispersing functionalized multi-wall carbon nanotubes in the PLGA polymer matrix. As shown in FIG. 8, scaffolds with 3% of MWCNT-COOH showed two-fold increase in compressive modulus and almost three-fold increase in compressive strength.

Example 4

Figure 9:
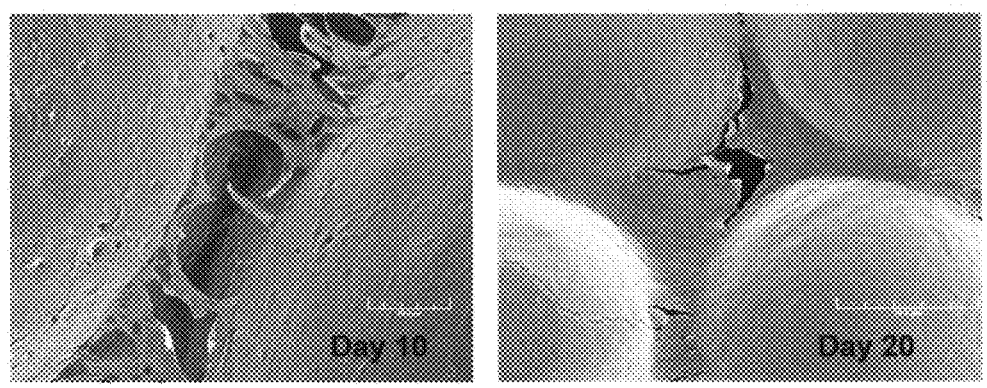
FIG. 9 is a pair of SEM images of pre-osteoblast (MC3T3-E1) cell proliferation on PLGA-3% CNT-COOH composite scaffolds recorded on 3D matrices cultured for 10 days and 20 days. By day 10, cells showed well spread morphology and by day 20, a confluent layer on the composite scaffold surface was observed.
Figure 10:
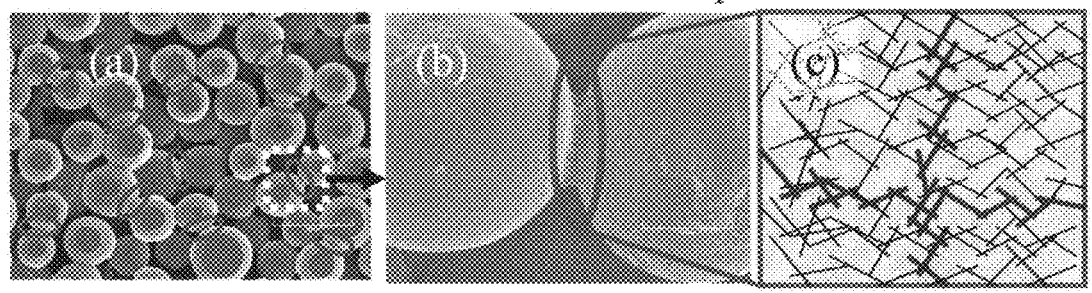
FIG. 10 shows that a scaffold compressive modulus and strength can be controlled by the percentage of carbon nanotubes present on the microsphere surface. Based on the observed mechanical enhancement, carbon nanotube content in the PLGA matrix can be adjusted according to needs.

Osteoblast Adhesion and Growth on 3D Composite Scaffolds (FIG. 9)

Mouse MC3T3-E1 osteoblasts were seeded onto 3D composite matrices at a density of $5 \times 10^4$ cells per each rounded scaffold of 8 mm diameter×2 mm thickness. A pilot study was conducted to see the cell adhesion and growth on 3D-composite scaffolds. Cellularized scaffolds at days 10 and 20 were taken out of the culture and processed using a standard procedure (Biomacromolecules (2008) 9: 1818-25). SEM investigations revealed the presence of cells on these composite scaffolds. Well-spread morphology was evidenced by day 10 with higher number of cells located at the microsphere-microsphere adjoining areas. Further, scaffolds cultured for 20 days showed a confluent layer of cells indicated the progressive growth of osteoblast cells on 3D scaffolds comprising 3 wt % of multi-wall carbon nanotubes.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A biocompatible composite scaffold material comprising sintered microspheres, wherein the microspheres comprise a biodegradable polymer and about 5% or less (wt/wt) water-dispersible carbon nanotubes sintered to microspheres at joining areas between adjacent microspheres.

2. The biocompatible composite scaffold material of claim 1, wherein the biodegradable polymer is poly(lactic acid-glycolic acid) (PLGA).

3. The biocompatible composite scaffold material of claim 2, wherein the PLGA has a lactic acid to glycolic acid ratio of about 85:15.

4. The biocompatible composite scaffold material of claim 1, wherein the biocompatible composite scaffold material comprises about 3% or less (wt/wt) functionalized carbon nanotubes.

5. The biocompatible composite scaffold material of claim 1, wherein about 1% to about 5% of the carbon atoms of the water-dispersible carbon nanotubes are functionalized with carboxyl groups, amide groups, hydroxyl groups, polyethylene glycol (PEG), or a combination thereof.

6. The biocompatible composite scaffold material of claim 1, wherein the carbon nanotubes are multi-wall carbon nanotubes.

7. The biocompatible composite scaffold material of claim 1, comprising about 3% or less (wt/wt) functionalized carbon nanotubes; wherein the biodegradable polymer comprises poly(lactic acid-glycolic acid) (PLGA).

8. The biocompatible composite scaffold material of claim 7, wherein the carbon nanotubes are functionalized with carboxyl groups, amide groups, hydroxyl groups, polyethylene glycol (PEG), or a combination thereof.

9. The biocompatible composite scaffold material of claim 7, wherein the carbon nanotubes are multi-wall carbon nanotubes.

10. The biocompatible composite scaffold material of claim 1, further comprising a bioactive agent selected from the group consisting of: bone morphogenic proteins (BMPs), vascular endothelial growth factor (VEGF), connective tissue growth factor (CTGF), osteoprotegerin, growth differentiation factors (GDFs), cartilage-derived morphogenic proteins (CDMPs), LIM mineralization proteins (LMPs), transforming growth factor β (TGFβ), antibiotics, immunosuppressive agents, and combinations thereof.

11. The biocompatible composite scaffold material of claim 1, wherein the porosity of the scaffold is at least 30%.

12. A method of effecting bone repair comprising contacting the area affected by a bone defect with the biocompatible composite scaffold material of claim 1.

13. The method of claim 12, wherein the biodegradable polymer is poly(lactic acid-glycolic acid) (PLGA).

14. The method of claim 12, wherein the biocompatible composite scaffold material comprises about 3% or less (wt/wt) functionalized carbon nanotubes.

15. The method of claim 12, wherein at least 4% of the carbon nanotubes are functionalized with carboxyl groups, amide groups, hydroxyl groups, polyethylene glycol (PEG), or a combination thereof.

16. The method of claim 12, wherein the biocompatible composite scaffold material further comprises a bioactive agent selected from the group consisting of: bone morphogenic proteins (BMPs), vascular endothelial growth factor (VEGF), connective tissue growth factor (CTGF), osteoprotegerin, growth differentiation factors (GDFs), cartilage-derived morphogenic proteins (CDMPs), LIM mineralization proteins (LMPs), transforming growth factor β (TGFβ), antibiotics, immunosuppressive agents, and combinations thereof.

* * * * *